United States Patent [19]
Cowsar et al.

[11] Patent Number: 5,565,216
[45] Date of Patent: Oct. 15, 1996

[54] HAIR RELAXER COMPOSITIONS

[75] Inventors: Donald R. Cowsar, Savannah; Tony R. Adair, Tybee Island, both of Ga.

[73] Assignee: Carson Products Company, Wilmington, Del.

[21] Appl. No.: 93,956

[22] Filed: Jul. 21, 1993

[51] Int. Cl.⁶ ..................................................... A61K 7/09
[52] U.S. Cl. ........................................... 424/704; 424/702
[58] Field of Search ................................ 424/71, 702, 704

[56] References Cited

U.S. PATENT DOCUMENTS

| | | | |
|---|---|---|---|
| 4,303,085 | 12/1981 | de la Guardia et al. | 132/7 |
| 4,304,244 | 12/1981 | de la Guardia | 132/7 |
| 4,314,572 | 2/1982 | de la Guardia | 132/7 |
| 4,324,263 | 4/1982 | de la Guardia | 132/7 |
| 4,373,540 | 2/1983 | de la Guardia | 424/89 |
| 4,390,033 | 6/1983 | Khalil et al. | 132/7 |
| 4,416,296 | 11/1983 | Meyers | 132/7 |
| 4,524,787 | 7/1985 | Khalil et al. | 132/7 |
| 4,680,300 | 7/1987 | Nelson et al. | 514/312 |
| 4,898,726 | 2/1990 | Beste | 424/72 |
| 4,950,485 | 8/1990 | Akhtar et al. | 424/71 |
| 5,068,101 | 11/1991 | Akhtar et al. | 424/71 |
| 5,077,042 | 12/1991 | Darkawa et al. | 424/71 |

FOREIGN PATENT DOCUMENTS

| | | |
|---|---|---|
| 2410678 | 9/1974 | Germany. |
| 8909048 | 10/1989 | WIPO. |
| 9104007 | 4/1991 | WIPO. |

*Primary Examiner*—Jyothsna Venkat
*Attorney, Agent, or Firm*—Sughrue, Mion, Zinn, Macpeak & Seas

[57] ABSTRACT

The present invention relates to a two-component hair relaxer system comprising (a) a first component comprising a cream base containing a water-soluble salt of a relatively strong base with an anion capable of being precipitated by an alkaline earth metal ion under highly alkaline conditions, and (b) a second, separate component, which is substantially free of water, and containing an alkaline material having an alkaline earth metal ion which forms a precipitate with the anion when the first component and second component are mixed.

56 Claims, No Drawings

HAIR RELAXER COMPOSITIONS

FIELD OF THE INVENTION

The present invention relates to a two-component hair relaxer system which produces a highly alkaline hydroxide relaxer upon mixing of the two components, and to a process for making the relaxer. More particularly, the present invention relates to a two-component system in which the concentration of the highly alkaline hydroxide in the relaxer can be accurately controlled when less than a full kit volume is used. Further, the present invention is directed to a hair relaxer system with improved product stability and shelf life.

BACKGROUND OF THE INVENTION

Aqueous highly alkaline hair relaxer (straightener) compositions are known in the art in the form of alkaline, oil-in-water emulsions which derive their chemical activity from either (1) alkali metal hydroxides, (2) quaternary ammonium hydroxides, or (3) guanidine hydroxide dissolved or suspended in the water phase of these hair-treatment compositions such that the pH values of these emulsions are in the range of from 12 to 14 ("highly alkaline"). It is widely and generally accepted that it is the hydroxide ion, which is the alkaline chemical species common to all three of the above classes, that is the essential active ingredient in these "strong base" relaxers. It has been proven that hydroxide ions, when inside the cortex of the hair, readily extract acidic alpha protons from the cysteine moieties of hair keratin leading to reversible beta elimination of alkyl disulfide (opening of cross-links) with the concomitant formation of dehydroalanine. As these crosslinks continuously open and reform, the curly hair is relaxed to a permanently straight configuration.

Although it is the hydroxide anion which is responsible for initiating the chemical reactions within the hair shaft which lead to straightening, it is the cation with which the hydroxide is associated that distinguishes the various known highly alkaline relaxer types from each other. Prior to 1979, one-component ("no-mix") highly alkaline hair relaxer compositions deriving from either sodium or potassium hydroxides were known. In 1979, a mix-type "no-lye" relaxer containing guanidine hydroxide was introduced. A no-lye relaxer is one that does not contain sodium or potassium hydroxide. Because guanidine hydroxide is not stable for long periods in aqueous solutions, it must be prepared fresh just prior to using. Guanidine hydroxide is generally prepared by mixing an inorganic alkaline earth hydroxide with an aqueous solution of a salt of the strong organic base guanidine, where the anion of the salt is capable of being precipitated by the cation of the alkaline earth hydroxide. In commercially available products of this type, the guanidine hydroxide is generally prepared using calcium hydroxide and guanidine carbonate.

Two-component systems for the preparation and use of guanidine hydroxide relaxers are well documented in the patent literature, as disclosed, for example, in U.S. Pat. No. 4,304,244. The first component comprises a viscous cream base containing calcium hydroxide and the second component, known as an activator, comprises an aqueous solution of guanidine carbonate. The two components are combined to form an activated cream containing guanidine hydroxide. U.S. Pat. No. 4,304,244 discloses a two-component composition, and states that one or both of the components may be in the form of an aqueous solution, or both components may be in a non-aqueous form with water additionally added to the admixed components. The patent states that when a two-component system is used, the individual components may vary from a solid component to a very dilute solution or dispersion. The patent states that it is decidedly preferred that the hydroxide component and guanidine salt be packaged as separate components, especially with each component in the form of an aqueous solution, as the resulting mixing of the components is greatly facilitated thereby. All of the examples which employed a two-component system used a cream base containing an alkaline earth metal hydroxide (e.g., calcium hydroxide) and a guanidine carbonate solution in a weight ratio of at least 70% cream base to 30% guanidine carbonate solution.

The volume of liquid activator in the commercially available two-component systems is typically 50 to 80 ml, and is contained in a container or bottle with a narrow mouth to facilitate pouring. The volume of the cream base is generally 200 to 220 ml and is contained in a wide-mouth container to facilitate the stirring process when the liquid activator is poured into the cream base. Both the cream base and the liquid activator have a significant amount of water present.

The liquid activator contains a sufficient amount of water to ensure that the guanidine carbonate is completely dissolved in the activator. The guanidine carbonate is typically present in the activator in a high concentration of 20 to 30% by weight. The cream base, which is an oil-in-water emulsion, typically contains about 40 to 60 weight percent water, and 4 to 7 weight percent calcium hydroxide. The calcium hydroxide generally is present in a molar excess with respect to the guanidine carbonate. The cream base to liquid activator weight ratio is generally at least about 3-to-1 to 6-to-1. The cream base and liquid activator each have a density of about 1, and thus the cream base to liquid activator volume ratio also is generally about 3-to-1 to 6-to-1.

The activator to be added to the cream base contains a significant amount of water in relation to the total amount of water present in the two components, and the cream base is usually formulated to be viscous so that when the additional water from the liquid activator is added to the cream base, the resulting admixed relaxer will have a manageable consistency and will not become runny. The viscous cream base, in itself, however, is thick and difficult to stir. Moreover, the large difference in rheologies between the cream base and liquid activator makes it more difficult to uniformly mix the activator with the cream base. Mixing times for conventional two-component systems are typically long, on the order of two to four minutes, depending on the age of the cream base.

A food coloring is sometimes added to the activator so as to provide the consumer with visual feedback on the degree of mixing of the liquid activator and the cream base. For example, if red food coloring is added to the liquid activator, when mixed with a white cream base, the consumer will be directed to achieve a uniform pink color.

The two-component systems currently in use present a number of problems for the consumer. The existing two-component systems are most accurate when the user mixes all of the cream base supplied in the container with all of the concentrated liquid activator supplied in the bottle. Because these components are pre-measured to close tolerances by the manufacturer, the thorough mixing of full measures by the consumer results in relaxers whose chemical strengths are those designed by the manufacturer for different hair textures and types. Even when full measures are used, however, any accidental spillage (typically by splashing during mixing) of even a small amount of the concentrated liquid activator will yield a mixed relaxer having a lower strength than intended.

Another problem arises when the consumer uses only a portion of the relaxer kit at one time while saving the remaining product for later use. After having a relaxer treatment and as new hair grows, the consumer must relax the new growth to maintain the hairstyle. Because these touch-ups seldom require the entire amount of relaxer in a kit, the consumer typically will measure out and mix half of the contents of both the relaxer base cream container and the activator bottle. Then, the consumer saves the remaining unmixed components and uses them later for a second touch-up.

In preparing a relaxer using less than the full contents of a kit, the consumer generally relies on estimates which the consumer makes of half measures, from pre-drawn lines on the cream base container and the liquid activator bottle. For example, the consumer must first measure out one half the contents of the cream base. In some relaxers this is accomplished by measuring out a predetermined number of level scoops. Of course, if the consumer does not use the scoop and attempts to estimate one half the contents of the cream base, there is a large likelihood of error. Even if the consumer is careful in measuring out the indicated number of scoops, the scoops may not be level, and the scoop may not be entirely emptied before refilling successive scoops.

Once having measured the one-half amount of cream base, the consumer must then measure out one half of the liquid activator containing guanidine carbonate. Such commercially available liquid activators typically contain a "half line" on the side of the bottle so that the consumer will know what is the half contents amount. Again, consumer errors in measuring amounts of activator are also common and difficult to avoid. Moreover, the half line is not always accurately placed on the bottle by the manufacturer, and the quantity of activator actually filled into the bottle may be over or under the intended amount due to mal-adjustment or malfunction of the high-speed filling equipment.

The problem arises that unless the consumer is extremely diligent in measuring out the one-half amounts of base and activator, the final guanidine hydroxide concentration in the mixture will greatly vary depending on whether the measured amounts are over or under the one-half target amount. It has been determined that consumer errors from measuring the base and/or activator can easily result in fluctuations of ±10% in the volume of cream base and ±10% in the volume of activator employed, resulting in fluctuations in guanidine hydroxide concentrations of ±10 percent or more, when the target amounts are half of the container contents. Measuring errors can be much greater when the estimated targets are other than half contents or when spillage occurs. These measuring errors of ±10% or more can lead to wide variations in strength which can yield poor results such as ineffective relaxing (e.g., the hair does not relax as much as it should) and premature reversion, when the concentration of guanidine hydroxide is too low, or excessive side effects such as scalp irritation, hair damage and hair breakage to the consumer, when the concentration of guanidine hydroxide is too high.

Typically, the cream base component of the two-component relaxer contains an excess of calcium hydroxide so that the reaction of the guanidine carbonate is driven to completion. It is therefore the amount of guanidine carbonate added to the cream base and the total volume of the final mixture that determines the concentration of the guanidine hydroxide in the product when it is applied to the hair. Measuring errors of components on the part of the consumer can greatly alter the concentration of guanidine hydroxide in the admixed product resulting in insufficient relaxation or damage from overprocessing.

In addition to these errors in measuring the amount of liquid activator and cream base, errors are also introduced when the two components are mixed together. In order to obtain a uniform concentration of guanidine hydroxide in all portions of the relaxing mixture, the consumer must thoroughly mix the measured amount of activator and cream base.

It has been observed that consumer errors in the mixing step are also common and difficult to avoid. For example, if the consumer mixes the activator with only the top portion of the cream base, without diligently mixing the contents at the bottom of the cream base container, the concentration of guanidine hydroxide at the top portion of the container will be significantly higher than at the bottom portion of the container. The concentration of guanidine hydroxide at the top portion can vary significantly from that designed by the manufacturer, and can be, for example, as much as two times greater than that designed by the manufacturer. The insufficient mixing by the consumer creates a concentration gradient in the admixed relaxer. Thus, the first half of the relaxer placed on the hair will be much stronger than the bottom half of the relaxer placed on the hair. This results in uneven relaxing and possibly damage to the hair.

U.S. Pat. No. 5,068,101 discloses a two-component system in which one component is an aqueous solution of about 25 to about 30 weight percent guanidine carbonate which serves as the liquid activator, and the other component contains about 4 weight % to about 7 weight % calcium hydroxide emulsified in a cosmetic cream base. About 3.5 to about 6 parts by weight of the cosmetic cream base are mixed with one part by weight of the activator to provide the guanidine hydroxide hair relaxer. U.S. Pat. No. 5,077,042 discloses a conditioning activator which is substantially a liquid comprising a relatively strong organic base and a highly alkaline, no-scalp-barrier- necessary, no-lye cosmetic cream containing calcium hydroxide.

These patents disclose the possibility that guanidine carbonate may be included in the emulsion of the cream base and calcium hydroxide may be added in the form of an aqueous suspension just before use. U.S. Pat. No. 5,077,042 describes this approach as being impractical, and states that the amount of calcium hydroxide required for the reaction would be difficult to suspend in liquid form and would likely result in a non-uniform reaction mixture which would not relax the hair properly. These patents do not disclose any example where the guanidine carbonate is in a cream base and the calcium hydroxide is in an aqueous suspension. These patents do not discuss the problem of consumer measuring and mixing errors.

As a result, these patents do not provide the consumer with a product which does not have the problems of variation in guanidine hydroxide concentration when mixed by the consumer.

Other problems associated with liquid activators include the possibility of spilling and splashing, which can affect the amount of activator that is added to the cream base. Spillage can cause stains, particularly if food coloring is present in the liquid activator.

Another problem in the art is the potential toxicity of the guanidine carbonate solution used to activate the relaxer cream. The relative toxicity of guanidine carbonate is well established in the literature. Currently, the guanidine carbonate solution used in a two-component relaxer is packaged in a child-resistant bottle to prevent accidental ingestion. However, given the volume of the solution (from 50 ml to 80 ml), it is possible that the entire contents of a bottle could be swallowed. Therefore, the potential for accidental ingestion and poisoning based on the small amount of liquid guanidine carbonate remains a problem.

Food coloring has been added to the activator in order to indicate the degree of mixing between the cream base and the activator. However, such a conventional type of indicator does not indicate that the guanidine carbonate has reacted with the calcium hydroxide. It merely shows the extent that the liquid activator has been physically mixed with the cream base.

Another problem in the art is that ammonia is formed over time in the guanidine carbonate aqueous liquid activator component due to the hydrolysis of the guanidine carbonate. The formation of ammonia in the guanidine carbonate aqueous liquid activator component causes an undesirable odor. Thus, the liquid activator itself is inherently unstable and has a relatively limited shelf-life.

A still further problem in the art is that relaxers are often irritating to the scalp of the user. When a consumer is also color treating the hair, which is also irritating to the scalp of the consumer, the consumer must wait for several weeks after the relaxer treatment to color the hair (and vice versa) in order to avoid further irritation.

SUMMARY OF THE INVENTION

Accordingly, an object of the present invention is to provide a two-component hair-relaxer system containing a cream base and activator which can provide a concentration of alkaline hydroxide in the resultant admixture that does not vary significantly, even when errors are introduced by the consumer during the step of measuring amounts of cream base and amounts of activator.

A further object of the present invention is to provide a two-component hair relaxer system which can provide a more uniform concentration of alkaline hydroxide in the resultant admixture that does not vary significantly, even when errors are introduced by the consumer during the step of physically mixing the cream base with the activator.

It is a further object of the present invention to provide a relaxer composition in which a potential toxic guanidine carbonate solution is present in a form which reduces the likelihood of accidental poisoning by ingestion.

Another object of the present invention is to provide two components for a relaxer composition which are easier for the user to mix together.

A still further object of the present invention is to provide a water-containing composition which contains a compound which is susceptible to hydrolysis and formation of ammonia in which the rate of formation of unwanted ammonia is reduced.

Another object of the present invention is to provide a relaxer that is not as irritating to the scalp and skin.

Yet another object of the present invention is to provide a relaxer composition which contains an indicator that provides the user with visual feedback that the cream base and the activator have successfully reacted to form an efficacious relaxer.

To achieve the foregoing objects and in accordance with its purpose, there is provided, in a first aspect of the present invention, a two-component hair relaxer system for producing an alkaline hydroxide relaxer for relaxing hair comprising (a) a first component comprising a water-containing cream base containing a water-soluble salt of a relatively strong base with an anion capable of being precipitated by an alkaline earth metal ion under highly alkaline conditions, and (b) a second, separate component, which is substantially free of water, comprising an activator containing an alkaline material having an alkaline earth metal ion which forms a precipitate with the anion when the first component and second component are mixed.

In a second aspect of the present invention, there is provided a water-containing composition which contains a water-soluble salt of a relatively strong nitrogen containing organic base with a carbonate anion and which salt is susceptible to alkaline hydrolysis and formation of ammonia, wherein the water-containing composition contains a carbonate/bicarbonate buffer to retard the decomposition and formation of ammonia.

In a preferred embodiment of the second aspect of the present invention, a pH indicator is present in the water-containing composition which contains a carbonate/bicarbonate buffer to provide the user with a reliable indication of the thoroughness of mixing by changing color when the water-soluble salt of the relatively strong nitrogen containing organic base with a carbonate anion has reacted with an alkaline material having an alkaline earth metal ion which forms a precipitate with the carbonate anion.

It is to be understood that both the foregoing general description and the following detailed description are exemplary and explanatory, but are not restrictive of the invention.

DETAILED DESCRIPTION OF THE INVENTION

In the first aspect of the present invention, there is provided a hair relaxer system of the present invention which comprises (a) a first component (the cream base) comprising a water-containing cream base containing a water-soluble salt of a relatively strong base with an anion capable of being precipitated by an alkaline earth metal ion under highly alkaline conditions, and (b) a second component (the activator) which is substantially free of water, and containing an alkaline material having an alkaline earth metal ion which forms a precipitate with the anion when the first component and second component are mixed.

The cream base of the present invention preferably is an oil-in-water emulsion and contains a water-soluble salt of a relatively strong base with an anion capable of being precipitated by an alkaline earth metal ion under highly alkaline conditions. The water-soluble salt is present in the aqueous phase of the oil-in-water emulsion.

The relatively strong base which forms the water-soluble salt is a base which provides a pH of between 12 and 14 when in an aqueous medium. The relatively strong base generally is an organic nitrogen containing base, and preferably is guanidine. Other organic bases which may be used in place of guanidine include N-methyl guanidine, dimethylaminoguanidine, acetamidine, dimethylaminoamidine, aminoamidine and acetamide.

The anion capable of being precipitated by an alkaline earth metal under highly alkaline conditions preferably is the carbonate ion. Thus, the preferred water-soluble salt is guanidine carbonate. Salts other than the carbonate salt, such as a sulfate, sulfite, phosphate, fluoride, oxalate, tartrate, laurate or alginate salt can be used.

The oil phase generally contains anhydrous, lipophilic ingredients, which include an oleaginous material and an emulsifier.

Any suitable oleaginous material can comprise the oil phase for the cream base emulsion. Suitable oleaginous materials include petrolatum, mineral oil and mineral jellies, but also can include vegetable and animal derived oils and fats, and like unctuous emulsifiable materials. Preferred oleaginous materials are mineral oil and petrolatum or a mixture of the two. Particularly preferred is a petrolatum-mineral oil mixture, where the petrolatum and mineral oil are present in approximately equal weight amounts. At least 50 weight percent, preferably about 55 to about 75 weight percent of the oil phase is comprised of the oleaginous material such as the mineral oil-petrolatum mixture.

The oil phase may further comprise emulsifiers, present in an amount of about 5 to about 18 weight percent of the cream base. Suitable emulsifiers include nonionic emulsifiers, anionic emulsifiers, cationic emulsifiers, and amphoteric emulsifiers.

Suitable nonionic emulsifying agents include fatty alcohols, polyoxyethylene derivatives of fatty acid esters of sorbitol and sorbitol anhydride; polyethylene glycol esters of fatty acids, polyoxyethylene ethers of fatty alcohols, polyethylene oxide-polypropylene oxide condensates and polyoxyethylene lanolin ethers, and the like.

Examples of preferred non-ionic emulsifiers include a mixture of fatty alcohols having about 12 to about 24 carbon atoms, preferably 14 to about 22 carbon atoms in the fatty carbon chain. Specific examples include cetyl alcohol, stearyl alcohol, Steareth-10, Steareth-20, PEG-5 Soya sterol, and PEG-10 Soya sterol. Other suitable emulsifiers which may be added to the oil phase include ceteareth-20 (a non-ionic emulsifier comprised of a polyethylene glycol ether of cetearyl alcohol, which is a mixture of cetyl and stearyl alcohol). Cosmowax J is a preferred non-ionic emulsifier, sold by Croda, Inc., New York, N.Y. Cosmowax J is comprised of 80% cetearyl alcohol and 20% ceteareth-20. Cetearyl alcohol is a mixture of fatty alcohols containing predominantly cetyl alcohol and stearyl alcohol. Ceteareth-20 is a non-ionic emulsifier comprised of a polyethylene glycol ether of cetearyl alcohol. The non-ionic emulsifier generally is present in an amount of about 6 to 14 weight percent, preferably 8 to about 12 weight percent of the cream base.

Suitable anionic emulsifying agents include polyoxyethylene oleyl phosphates, sodium lauryl sulfate, and the stearic acid anion and the like. Polyoxyethylene (3) oleyl ether phosphate is particularly preferred.

The oil phase comprises about 15 to about 55 weight percent, preferably about 25 to about 45 weight percent of the cream base. The oil phase of the cream base is emulsified with the aqueous phase of the cream base which is described as follows.

The aqueous phase of the cream base comprises water and the water-soluble salt of a relatively strong base (e.g., guanidine carbonate) which can be added in suitable amounts.

The concentration of water-soluble salt (e.g., guanidine carbonate) in the cream base is generally from 1 to 20% by weight, preferably from 2 to 15% by weight. More preferred concentrations of the water-soluble salt (e.g., guanidine carbonate) are from 1 to 10% by weight and most preferred is 6 to 8% by weight of the cream base.

The water may be present in the aqueous phase in amounts of 80 to 90 weight % and in the cream base in amounts of 40 to 60 weight %. Water preferably comprises at least 50 weight percent of the cream base.

One or more co-emulsifiers may be added to the aqueous phase of the cream base to improve the texture of the cream base and control viscosity. A particularly preferred co-emulsifier is PPG-12 PEG-65-Lanolin oil which is a polyoxypropylene, polyoxyethylene derivative of lanolin oil, such as sold under the tradename Fluilan AWS by Croda, Inc., New York, N.Y. Lanolin derivatives may be added in an amount of about 1 to about 3 weight percent of the cream base.

A conditioner may be added to the cream base as desired. Suitable conditioning agents include non-polymeric quaternary nitrogen containing compounds such as those taught in U.S. Pat. No. 5,077,042. Particularly preferred non-polymeric quaternary nitrogen containing conditioners include Finquat CT (Quaternium 75 sold by Fintex, Inc., Elmwood Park, N.J.) and Arquad 2HT-75 (Quaternium 18 manufactured by Akzo Chemical, Inc., Chicago, Ill.). Amounts of conditioner are preferably about 0.05 to about 5 weight percent, more preferably about 0.1 to about 4 weight percent of the cream base. Although polymeric quaternary nitrogen containing conditioners can also be used, they are not preferred for use in a guanidine carbonate-containing cream base of the present invention since they usually result in an unstable emulsion which separates upon aging and which must be remixed before use.

A surfactant may be added to the cream base as needed to enhance the rinsing of the relaxer from hair. The surfactant can comprise anionic or amphoteric compounds such as dioctyl sodium sulfosuccinate, lauroyl sarcosine, and cocoamphopropyl sulfonate.

Preferred surfactants for use with guanidine carbonate include Crodafos SG, Miranol C2M-SF, Miranol C2M, Sandopan DTC, and Duponol XL. Crodafos SG is PPG-5 ceteth-10 phosphate sold by Croda, Inc., New York, N.Y. Miranol C2M-SF is disodium cocoamphodipropionate sold by Miranol, Inc., Dayton, N.J. Miranol C2M is disodium cocoamphodiace-tate, also sold by Miranol. Sandopan DTC is sodium trideceth-7 carboxylate sold by Sandoz Chemical Corporation, Charlotte, N.C. Duponol XL is a surfactant containing DEA-lauryl sulfate, sodium lauraminopropionate and DEA-lauraminoproprionate, sold by DuPont Company, Wilmington, Del.

The surfactant may be present in the cream base in an amount of from 0.5% to 4%, preferably 1% to 3%, more preferably 1% to 2%, by weight of the cream base.

The cream base can also include cosmetic adjuvants, such as auxiliary emollients, auxiliary thickening agents, perfumes, preservatives, and product colorants.

The total amount of non-water components in the cream base preferably makes up no more than about 50% by weight of the total weight of the cream base.

In preparing a typical cream base component according to the present invention, guanidine carbonate is present in the cream base emulsion preferably in amounts of between 6 to 8 percent by weight. The guanidine carbonate may be added to the cream base as a dry powder. In preparing the cream base composition, the oil phase components and the water phase components without guanidine carbonate are heated in separate vessels to between 70° C. and 80° C. Then, the oil phase is added to the aqueous phase and homogenized at high speed for about 15 minutes to about 30 minutes. When the mixture has cooled to a temperature of about 45° C., the guanidine carbonate is added and stirring is continued while a conditioner, if desired, is added. Then the surfactant is added. Alternatively, the guanidine carbonate can be added to the water phase before the water phase is mixed with the oil phase.

The second component of the two-component relaxer system of the present invention is the activator, which is substantially free of water, and which contains an alkaline material having an alkaline earth metal ion which precipitates with the anion of the water-soluble salt present in the cream base. The alkaline material in the activator can be an alkaline earth metal hydroxide such as calcium hydroxide, barium hydroxide and strontium hydroxide, or an alkaline earth metal oxide, such as calcium oxide or barium oxide, which forms the corresponding alkaline earth metal hydroxide when placed in an aqueous medium, or a mixture of the alkaline earth metal hydroxide and alkaline earth metal oxide. Calcium hydroxide or a mixture of calcium hydroxide and calcium oxide is the preferred alkaline material in the activator of the present invention.

When the preferred calcium hydroxide activator is admixed with the preferred cream base containing guanidine carbonate prior to use, insoluble calcium carbonate and soluble guanidine hydroxide are formed.

The activator of the present invention, which is substantially free from water, is in the form of a powder or a lotion.

As used herein, the term "substantially free of water" means that small amounts of water of less than about 20 weight percent, preferably less than about 10 weight percent, can be present in the activator, as long as the water does not interfere with the ability of the activator to flow freely when in powder form or pour easily when in lotion form. Generally, it is preferred that no water be present in the activator so that the activator is anhydrous, but small amounts of from about 1 to about 20 weight percent can be tolerated.

When the activator is in the form of a powder, the powder can contain up to about 20 weight percent by water and still be a flowable powder. Greater amounts of water in the powder result in a thick, non-free flowing non-pourable mass up to about 50% water. At about 50% water and above, the alkaline material would be present as an aqueous suspension. When the activator is in the form of a lotion, the lotion can contain up to about 20% weight percent water without substantially affecting the properties of the lotion, but in amounts of more than about 20%, the water would change the viscosity of the lotion and the mixture would become an unpourable, unworkable semi-solid mass.

When in the form of a lotion, the activator is a viscous, pourable suspension which contains the alkaline material, such as alkaline earth metal hydroxide, for example, calcium hydroxide, generally in an amount of from 20 to 60 weight percent, preferably 30 to 55, most preferably from 40 to 50 weight percent. If the amount of alkaline material such as alkaline earth metal hydroxide in the lotion is more than 50 weight percent, the lotion does not pour well. The alkaline material such as alkaline earth metal hydroxide is present in the lotion in an amount sufficient to provide a molar excess of the alkaline material, such as alkaline earth metal hydroxide, with respect to the water-soluble salt of the cream base when mixed with the cream base. Generally, a molar excess of alkaline material (e.g., calcium hydroxide) of from about 5% to about 200% can be employed, more preferably 10 to 120%. It will be understood that the term "molar excess" as used herein refers to an amount of alkaline material which is in excess of the stoichiometric amount of alkaline material needed to react with the water-soluble salt.

The activator lotion contains a suitable water-miscible, hydrophilic liquid carrier to deliver the alkaline material (e.g., calcium hydroxide) present in the activator into the aqueous, continuous phase of the cream base emulsion, such as a guanidine carbonate containing cream base emulsion. Suitable carriers include polyhydroxy compounds (such as propylene glycol, glycerine, butylene glycol and hexylene glycol), and ethers including simple ethers and polyethers. A preferred carrier is propylene glycol. The propylene glycol also acts as a humectant in the hair to prevent dryness.

The amount of carrier in the lotion is preferably from 40 to 80% by weight, more preferably 50% to 60%.

Additionally, the activator lotion may contain a desiccant in order to remove any water that may be present in the activator and to maintain the activator lotion substantially anhydrous until the time of its use. Commercially obtained solid calcium hydroxide powder may sometimes contain small amounts of water, as shown by an off-white color, and the addition of a desiccant to the lotion, insures that the lotion will be substantially free of water. Suitable desiccants include simple anhydrides, polymeric anhydrides, or molecular sieves. A preferred desiccant is calcium oxide because it becomes calcium hydroxide when mixed with water.

The desiccant is generally present in the lotion in amounts of from 0 to 20% by weight, preferably 1% to 15%, more preferably 3 to 10%. When using calcium oxide as a desiccant, the amount thereof is included in the determination of the amount of alkaline material present in the activator.

The activator lotion may also contain a coloring agent or opacifying agent. Preferred coloring agents are pigments and dyes. Suitable pigments include metal oxide whiteners. A preferred whitener is titanium dioxide. The whitener is preferably present in the lotion in an amount of from 0.5 to 5% by weight.

In addition, the lotion activator may contain a thickener. Suitable thickeners include organic polymers such as hydroxypropyl cellulose and hydroxyethylcellulose, anhydrous aluminum silicate and hydrated magnesium aluminum silicate and colloidal clays. A preferred thickener is fumed silica. The thickener is preferably present in the lotion in amounts of from 1 to 6% by weight, more preferably, 2% to 5% by weight.

The activator lotion of the present invention is a phase-stable composition which when subjected to an accelerated aging test at 50° C. for 30 days shows no phase separation. The term "phase-stable" as used herein refers to the physical stability of the lotion. The phase-stable lotions of the present invention do not visibly separate when subjected to the above accelerated aging test. The above time period represents a commercially useful lifetime in the field, and the lotion is stable in the field for a period of at least one year.

When in the form of a powder, the activator powder comprises a powder or crystalline form of the alkaline material, such as solid calcium hydroxide powder or calcium oxide powder. The alkaline material (e.g., calcium hydroxide) preferably has a particle size such that >95% passes through a 325 mesh sieve. Amounts of alkaline material (e.g., calcium hydroxide) in the powder are preferably from 20 to 100% by weight, still more preferably from 60% to 90% by weight. A preferred amount of alkaline material (e.g., calcium hydroxide) in the powder is from a 5% to a 200% molar excess over the water-soluble salt (e.g., guanidine carbonate) in the relaxer cream base, more preferably a 10% to a 120% % molar excess.

A surfactant/wetting agent may be present in the activator powder in order to provide the powder in a non-dusty state (i.e., to promote its pourability) and to promote the dispersability of the powder in the cream base. The surfactant/wetting agent can be present in the powder in amounts of from 2 to 25% by weight, preferably 10 to 20% by weight. Suitable surfactants/wetting agents include nonoxynols, sorbitols, and alkyl pyrrolidones. A preferred surfactant for use in the activator when it is in the powdered form is Surfadone LP 100 (ISP, Inc., Wayne, N.J.). The powder can be prepared by mixing calcium hydroxide powder with the surfactant by methods well known in the art, such as ribbon blending.

Other inactive ingredients can be present in the powder, such as calcium carbonate which serves to prevent compaction of the calcium hydroxide powder particles.

In a preferred embodiment of the present invention, the activator is in the form of a lotion that is substantially free of water. This form is preferred from the standpoint of easier mixing because the activator lotion has a closer rheology to the cream base.

The ratio of alkaline material containing activator (such as alkaline earth metal hydroxide containing activator) to cream base is generally from one part by weight activator to about 6 to 30 parts by weight cream base, most preferably 10 to 15 parts by weight cream base. The density of the cream base is generally about 1 gm/ml. The density of the activator is generally from about 1.4 gm/ml (for a lotion activator) up to about 2.34 gm/ml for a powder activator. The volume ratio of activator to cream base is generally from about one part by volume activator to about 8 to 50 parts by volume cream base, such as 10 to 25 parts by volume cream base.

The use of an activator lotion or powder that is substantially free of water is designed to deliver to the relaxer composition the maximum amount of the alkaline material having an alkaline earth metal ion (e.g., calcium hydroxide or calcium oxide) possible with the least amount of added volume. Because the activator to be added to the cream base is substantially free of water, the total amount of water in the final mixture will be that delivered from the cream base, and will remain relatively unchanged regardless of the ratio of activator to cream base which the consumer uses. Moreover, because the activator is in the form of a powder or a lotion which contains a high concentration of the alkaline material, the volume of activator necessary to supply the desired amount of alkaline material is relatively small, especially as compared to the volume of cream base. Therefore, the total volume of the admixture of cream base and activator will not be substantially affected by errors in volume in the amount of the activator and in the amount of the cream base.

Because the cream base will contain a fixed concentration of guanidine carbonate, the concentration of guanidine hydroxide in the product applied to the hair will remain relatively constant. Excess calcium hydroxide added to the base would remain insoluble and therefore, not have an appreciable effect on the concentration of the guanidine carbonate in the admixture.

In the conventional prior art method, a guanidine carbonate liquid activator is added to a calcium hydroxide cream base. Because the concentration of guanidine carbonate in such a relaxer is a function of the volume and concentration of the activator and the volume of the base, and because the activator is present in a volume amount of usually ⅓ to ⅙ the volume of the cream base, measuring errors in the amount of activator greatly affect the concentration of guanidine carbonate in the relaxer. The concentration of guanidine carbonate (Cr) (gm/ml) in the relaxer when the guanidine carbonate is supplied from a liquid activator as in the prior art can be defined by the following equation (Eq. 1):

$$Cr = \frac{Va \times Ca}{Va + Vb} \qquad (Eq.\ 1)$$

where

Va=volume of activator

Ca=concentration of guanidine carbonate in the activator (gm/ml)

Vb=volume of base

It can be seen that measuring errors can affect the volume of activator and volume of base. Because the activator is in the form of a concentrated aqueous solution in the prior art and is present in a volume amount of usually about ⅓ to about ⅙ the volume of the cream base, the amount of activator used has a large effect on the total volume of the admixture and thus the concentration of guanidine carbonate (Cr) in the relaxer.

In the present invention, however, the guanidine carbonate is present in the cream base at a fixed concentration and the calcium hydroxide in the activator is substantially free of water. The concentration of guanidine carbonate (Cr) (gm/ml) in the relaxer when the guanidine carbonate is supplied in the cream base according to the present invention can be defined by the following equation (Eq. 2):

$$Cr = \frac{Vb \times Cb}{Vb + Va} \qquad (Eq.\ 2)$$

where

Vb=volume of cream base

Cb=concentration of guanidine carbonate in cream base (gm/ml)

Va=volume of activator

Because the volume amount of activator is usually 1/50 to ⅛ the volume amount of cream base, when the activator is added to the cream base, the effect of the activator on the total volume is very small. As a result, errors in the amount of activator and cream base do not result in significant errors in the final concentration of guanidine carbonate, when only a part of the cream base is measured out by the user.

In the present invention, if the consumer adds the activator properly but fails to mix the relaxer thoroughly from top to bottom, the concentration of the alkaline guanidine hydroxide in the top portion will not exceed the intended concentration. Because hair damage and scalp irritation can be serious consequences of using a too-strong relaxer preparation, the present invention has very significantly improved the safety of these mix-type relaxers.

In the two-component system of the present invention, the rheology of the two components is more closely matched than conventional two-component mix systems, and the mixing shear is improved. Further, the present system does not use an aqueous free-flowing liquid activator, and thereby reduces problems such as splashing and spillage of the activator and viscosity differences between activator and cream base. In addition, because the activator is substantially free of water, more water may be present in the cream base which results in a softer consistency for the cream base. This softer consistency makes it easier for the consumer to mix the activator into the base.

The provision of guanidine carbonate in a cream base emulsion reduces the likelihood of accidental ingestion of a toxic amount of guanidine carbonate because the guanidine carbonate is present in the cream base in a lower concentration than in prior art liquid activators, and the volume of cream base which contains the guanidine carbonate is significantly higher than the volume of prior art liquid activator compositions employed in a two-component system. Thus, if one were to ingest the same volume amount of cream base as liquid activator, then one would be receiving a lower dosage of the guanidine carbonate. Moreover, the volume of cream base which would be present in a two-component relaxer system of the present invention is so large that it is highly unlikely that a child would accidentally ingest an amount which is sufficient to be toxic. Further, the prior art liquid activators are in the form of a solution which is easier to ingest than a cream base.

In a second aspect of the present invention, there is provided a water-containing composition which contains a water-soluble salt of a relatively strong organic nitrogen containing base with a carbonate anion and which is susceptible to alkaline hydrolysis and formation of ammonia, wherein the water-containing composition contains a carbonate/bicarbonate buffer to retard decomposition of the water-soluble salt and formation of ammonia. The carbonate/bicarbonate buffer is present in the composition in an amount which provides the composition with a pH of from about 9.5 to 10.5.

The water-containing composition which is provided with the carbonate/bicarbonate buffer can be the cream base component of the first aspect of the present invention and wherein the water-soluble salt of the first aspect of the present invention is a water-soluble salt of a relatively strong organic nitrogen containing base with a carbonate anion and which is susceptible to alkaline hydrolysis, or can be a liquid activator such as used in the prior art wherein the liquid activator comprises a water solution of a water-soluble salt of a relatively strong organic base with a carbonate anion (such as guanidine carbonate), and which is susceptible to alkaline hydrolysis and which is present in an amount of about 20 to 30% by weight. Such a liquid activator can be a conventional liquid activator such as described in U.S. Pat. No. 4,304,244 and can contain conventional additives such as polyhydroxy compounds, thickening agents, metal-ion chelating agents, preservatives and perfume and can be used with conventional cream bases containing an alkaline material which reacts with the water-soluble salt, such as described in U.S. Pat. Nos. 4,304,244, 5,068,101 and 5,077,042.

For purposes of illustration only, the following description of the second aspect of the present invention will be based on the use of guanidine carbonate as the water-soluble salt, but is equally applicable to carbonate salts of any of the other organic nitrogen containing bases which have previously been described.

The pH of a cream base of the first aspect of the present invention containing guanidine carbonate is about 11.5 to 12. The guanidine carbonate in this cream base slowly decomposes over time at ambient temperature to liberate ammonia due to hydrolysis with the water present in the cream base. A strong objectionable ammonia odor is formed when such a cream base is packaged. Similarly, the guanidine carbonate liquid activators of the prior art have a pH of about 11.2 to 12.0 and also suffer from decomposition and formation of ammonia odor due to hydrolysis with water.

It has now been found in accordance with the second aspect of the present invention that the decomposition and formation of ammonia at ambient, and elevated temperature can be retarded by lowering the pH of the water-containing component (which for ease of explanation is referred to hereafter as the guanidine carbonate component) which contains the water-soluble carbonate salt of a relatively strong organic nitrogen containing base and which is susceptible to alkaline hydrolysis and formation of ammonia to about 10.5 or less, preferably to about 9.5 to 10.4.

In order to lower the pH of the guanidine carbonate component, a carbonate/bicarbonate buffer is created in the guanidine carbonate component by the addition of a suitable proton donor, such as by the addition of guanidine bicarbonate. When 5 to 10 mole percent of the guanidine carbonate is present as guanidine bicarbonate, the pH remains below a value of 10.4.

Guanidine bicarbonate may be added directly to or substituted for the guanidine carbonate in the guanidine carbonate component in an amount of from 0.4 to 5 percent by weight of the guanidine carbonate component or may be formed in situ by adding other relaxer components in their acid form.

Another method for lowering the pH of the guanidine carbonate component (either cream base or liquid activator) is to add a suitable acid to the guanidine carbonate component. A suitable acid is one that lowers the pH of the guanidine carbonate component without interfering with the relaxing process. An indication that the acid has interfered with the relaxing process is when excessive reversion occurs. An acceptable amount of reversion for a commercial product generally is about 15% or less, preferably less than 10%. Reversion is measured by the procedure in Example 4. For best results, the acid should not cause a degree of reversion of more than 10%.

The acid which is used may be an organic acid or an inorganic acid. Examples of suitable organic acids include aliphatic acids, alicyclic acids, aromatic acids and heterocyclic acids. These acids may be substituted. Examples of suitable substituents include an amino group and a hydroxy group. Suitable acids include monocarboxylic acids and dicarboxylic acids. Suitable dicarboxylic acids include substituted and unsubstituted aliphatic dicarboxylic acids, such as succinic acid, maleic acid, oxalic acid, and glutamic acid. Suitable monocarboxylic acids include substituted and unsubstituted aliphatic monocarboxylic acids, such as lactic acid. Suitable inorganic acids include sulfuric acid and phosphoric acid.

Preferred acids include succinic acid, maleic acid and glutamic acid.

In general, the amount of acid in the water-containing composition of the second aspect of the present invention is from about 5 to 20 mol%, preferably 5 to 10 mol%, of the number of mols of water-soluble carbonate salt (e.g., guanidine carbonate) in the water-containing composition.

In the preferred method for preparing the cream base containing the acid, the guanidine carbonate is first dissolved in the aqueous phase of the cream base, and then the acid component is added to form the carbonate/bicarbonate buffer.

Ammonia is formed at ambient or elevated temperatures due to the presence of hydroxide ions when the pH of the guanidine carbonate component is around 11.2 to 12, but it surprisingly has been found that by lowering the pH in the guanidine carbonate component of a two-component relaxer system to about 10.5 or less, the rate of formation of ammonia at ambient and elevated temperature is greatly reduced.

Surprisingly, in accordance with the second aspect of the present invention, it has also been discovered that lowering the pH of the guanidine carbonate component to retard ammonia formation significantly reduces skin and scalp irritation when the admixed relaxer composition is applied. The present invention has discovered that free ammonia is a significant contributor to skin and scalp irritation in guanidine-based relaxer systems. The fact that ammonia is a significant contributor to scalp irritation was not previously known in the art, and it was generally believed that the side-effects of stinging and burning sensations were principally caused by the guanidine hydroxide.

Further, it has been discovered that ammonia causes stinging and burning sensations even when present in the shampoo component that is applied to neutralize the relaxer after it has been rinsed from the hair. Accordingly, in a preferred embodiment of the present invention, a neutralizing shampoo is employed which does not contain any component which is subject to alkaline hydrolysis and formation of ammonia.

In a further embodiment of the second aspect of the present invention, a pH indicator is present in the water-containing composition of the second aspect of the present invention, which contains a carbonate/bicarbonate buffer in order to provide an indication to the user of the thoroughness of the mixing of the cream base and the activator. The color change of the pH indicator signals that a pH increase has occurred when the guanidine carbonate reacts with the calcium hydroxide. Thus, a uniform color change not only indicates thorough mixing but actually signals the presence of guanidine hydroxide so that the consumer knows that the ingredients of the product are active and that a working relaxer is present. The pH indicator can be present either in the cream base of the present invention which is provided with a pH of about 9.5 to 10.5, or in the guanidine carbonate liquid activator of the prior art.

A pH indicator would not work with a conventional two-component system of the prior art because there is an insufficient pH gradient between the pH of the conventional calcium hydroxide cream base (generally about 12.2 to 12.5) and the mixing pH of the admixed relaxer (generally about 13.5 to 13.7). High-pH indicators typically require a pH gradient of at least two.

In the second aspect of the present invention the guanidine carbonate component is provided with a pH of about 9.5 to 10.5, and a pH of the admixed relaxer is about 13.5 to 13.7, so that there is a sufficient pH difference which permits the use of known pH indicators. Therefore, standard pH indicators known to those skilled in the art can be used to provide the user with feedback as to the degree of mixing. In particular, a uniform color change will indicate thorough mixing. Suitable pH indicators include Tropaeolin "O" (also known as, Acid Orange 6), Thiazole Yellow "G", Alizarine Yellow R, and Metachrome Yellow. Other pH indicators that are suitable for use in the present invention include Eosin I, Poirriers Blue, Mordant Blue #1, Mordant Red #3, and External D&C Violet #2.

The pH indicator is typically added in an amount of from 0.0005% to 0.5% by weight, preferably 0.0008 to 0.01, most preferably 0.0015 to 0.005% by weight of the water-containing composition.

Preferably a kit for a conditioning hair relaxer system embodying the principles of this invention comprises at least two packages. For example, a first package can include the cream base component (e.g., the guanidine carbonate containing cream base) as described above. A second package can include the activator component (e.g., the calcium hydroxide containing activator). The contents of the first and second packages are admixed to provide an active relaxer composition just prior to use. In order to further minimize measuring errors, the activator component can be packaged in two separate packages, with each package containing one half of the total activator component. Then, when a consumer wishes to use the full contents of the kit, the consumer will empty the contents of both packages containing the activator composition into the contents of the first package. When the consumer wishes to use the half content of the kit, the consumer will measure out half the content of cream base package in a conventional manner and then empty one of the packages containing the activator into the measured half content of the cream base package. Since a single activator package contains exactly one half of the full amount of activator composition, no measuring error with respect to the activator is possible. The activator can be formulated to contain a 100% or greater molar excess of alkaline material, such as a 110% molar excess. If the activator component is then packaged in two separate packages, each package will contain the necessary number of moles to react with the full content of the cream base package. Thus, even if a consumer mistakenly uses a single package of activator with the full contents of the cream base package, there will be sufficient alkaline material to react with all of the water-soluble salt in the cream base.

The time of treatment of hair to be relaxed with the relaxer formulation of the present invention will normally be within the range of 5 to 45 minutes, starting from the first application of the relaxer composition to the hair. Generally, this treatment time will be at least 10 minutes, and there is normally no real upper limit on the time that the composition can remain on the hair. It is preferred to treat the hair for no more than about 30 minutes, preferably less than 25 minutes, and more preferably around 20 minutes.

After the above treatment time has elapsed, the relaxer composition should be removed from the hair in order to prevent damage to the treated hair. A major portion of the relaxer composition can be removed from the hair by thorough rinsing. It is preferred that the rinsing be followed by a neutralizing step, using any suitable agent that will neutralize alkali.

Further details of how to use a relaxer are disclosed in U.S. Pat. No. 4,373,540, which patent is hereby incorporated by reference.

The two-component relaxer system of the present invention provides numerous beneficial properties, which include low or no chemical odor, no-mistake lotion or powder activator, much easier mixing, very minimal scalp irritation, if any, faster working formula, more effective straightening of resistant hair, no relaxer smell left in hair, and very minimal reversion. Because the two-component relaxer system of the present invention substantially eliminates and reduces the problems caused by user measuring/mixing errors, it is highly reliable in that it always gives the same predictable good results each time the two-component relaxer system is used.

In the two-component hair relaxer system of the present invention, the water-soluble salt of a relatively strong base with an anion capable of being precipitated by an alkaline earth metal ion is the strength-determining chemical, and is formulated in the relaxer cream base at precisely the concentrations required for different hair types and textures; whereas, in the prior art it was contained in the liquid activator. The activator of the present invention is a super concentrate so that a small amount of the activator is all that is required to react with the water-soluble organic salt in the base. Using more of the activator than is the minimum required to react with the water-soluble salt of the cream base does not substantially affect the relaxer's strength or the results on the hair and scalp. Because the activator contains an excess of the alkaline material, the chance that too little of the activator will be used is highly remote.

It is, of course, important that the consumer stir/mix the activator and the cream base thoroughly to bring about the desired reaction. The new relaxer base has been designed to ensure good mixing results. First, the new base is very light, smooth, and creamy, and it can be stirred with ease. Second, the relaxer base preferably contains a color signal component that appears automatically as the base is stirred signalling that the water-soluble salt in the cream base has been reacted with the activator.

In the following examples, all amounts are by weight unless otherwise indicated.

EXAMPLE 1

A two-component hair relaxer system according to the present invention was formulated, with one component being in the form of a cream base and the other component being in the form of a lotion. The components had the following compositions.

| Formulation of Relaxer Base Containing | |
|---|---|
| Oil Phase | Weight Percent |
| Guanidine Carbonate. | |
| Oil Phase | |
| Cosmowax J | 12.00 |
| Petrolatum | 10.00 |
| Light Mineral oil | 10.00 |
| PEG-5 Soya Sterol | 1.00 |
| (sold under the name Generol 122E-5 by Henkel Corp., Hoboken, N.J.) | |
| Water Phase | |
| Deionized Water | 54.7985 |
| PPG-12 PEG-65-Lanolin Oil | 3.00 |
| (sold under the name Fluilan AWS by Croda, Inc.) | |
| Guanidine Carbonate | 7.40 |
| Succinic Acid | 0.30 |
| Thiazole Yellow "G" | 0.0015 |
| (sold by Pylam Products Co., Inc., Garden City, New York) | |
| PPG-5-Ceteth-10 Phosphate | 1.50 |
| (sold under the name Crodafos SG by Croda Inc.) | |
| | 100.00 |

The pH of the relaxer base is 10.1.

| Formulation of Activator Containing Calcium Hydroxide | |
|---|---|
| Propylene Glycol | 51.0 |
| Silica (Cabosil M5 sold by Cabot Corp., Tuscola, IL) | 4.0 |
| Calcium Hydroxide | 37.0 |
| Calcium Oxide | 6.0 |
| Titanium Dioxide | 2.0 |

The density of the activator lotion is 1.429 grams per milliliter.

To prepare the cream base, the components of the oil phase are placed together in a heatable vessel, and are heated to between 75° and 80° C.

In a separate heatable vessel, the above components of the water phase are added, and homogenized. The Fluilan AWS should be heated to 60° to 65° C. before it is added to the heatable vessel. The guanidine carbonate is thoroughly dissolved in the water phase, and then succinic acid is added to the water phase.

The vessel containing the water phase is then heated quickly to 70° C., and the heated oil phase is then added slowly to the water phase with moderate homogenization. The resulting emulsion is homogenized for 15 minutes more with moderate agitation. The homogenized emulsion is then transferred to a cooling vessel where it is with stirring cooled to 50° C. At 50° C., the Crodafos SG can be added, and mixing and cooling continue. The Thiazole Yellow G (a color indicator) can be added when the temperature reaches 45° C., and mixing is continued.

To prepare the activator, propylene glycol is placed in a homomixer and then moderately agitated. To the propylene glycol is slowly added the Cabosil M5 and mixed at high shear for approximately 30 minutes or longer until fully dispersed. Then, the calcium hydroxide and calcium oxide are added to the batch and mixed for approximately 25 minutes or until uniform. Next, the titanium dioxide is added and mixing is continued for 35 minutes to obtain the activator lotion.

To form the hair relaxer, the cream emulsion and the activator paste are admixed under ambient conditions in a weight ratio of 12.5:1 of cream emulsion:activator lotion. A spatula can be used to form a well in the cream emulsion, and the lotion added to the cream. The spatula is used to mix the cream base and activator lotion together thoroughly, scraping the sides and bottom of the mixing container, until the resulting relaxer composition is creamy and has a uniform color, free of streaks. This mixing takes about 2 minutes.

The hair of an individual to be treated is gently combed to remove tangles, and then the hair is sectioned, and a generous amount of the relaxer formulation is applied to the hair on a section-by-section basis. The hair is combed gently after the relaxer is applied to ensure even distribution, with care taken to avoid pulling or stretching the hair. When the entire head appears to be covered by the relaxer cream formulation, the hair is parted with a comb in different areas of the head and checked to ensure that the relaxer formulation has penetrated to the hair root area. Thereafter, all of the hair is smoothed down, from front to back, using hands or the back of a plastic comb.

The timing of the length of hair relaxer application is started from the moment of first application of the relaxer formulation, and the hair is treated for 15–20 minutes. For coarser textures than the medium textured individual tested, the maximum recommended time would be 20–25 minutes, whereas for individuals with finer hair, a treatment time of 10–15 minutes might suffice. It has generally been noted that porous hair or hair that has been colored requires less time than untreated hair.

After the desired treatment time had elapsed, the hair is rinsed thoroughly with warm water and the hair is then neutralized to approximately a neutral pH by shampooing with a buffered neutralizing shampoo.

The neutralizing shampoo has a pH of 4 to 5, a buffer capacity of 0.1 to 0.2 milliequivalents of 0.10N NaOH per gram of shampoo, and is substantially free of ammonia and ammonium ions.

The shampooing involves two lather and rinse cycles, and after the shampooing step the hair is optimally treated with a protein conditioner. After a final rinse the hair is towelled dry and set.

The hair treated in this example has a permanent relaxing or straightening effect, which lasts until new growth appears at the hair roots. The application of this relaxer composition to the individual's scalp, ears, and other parts of the body results in reduced complaints of skin irritation and burning sensations.

EXAMPLE 2

A two-component hair relaxer system according to the present invention was formulated with the following composition for the cream base.

| Formulation of Relaxer Base Containing Guanidine Carbonate | |
|---|---|
| Ingredient | Weight % |
| Oil Phase | |
| Cosmowax J | 10.50 |
| Mineral oil | 10.75 |
| Petrolatum | 10.75 |
| PEG-5 Soya Sterol (Generol 122E-5, sold by Henkel Corp.) | 1.00 |
| Water Phase | |
| Deionized Water | 55.7512 |
| Fluilan AWS | 3.000 |
| Guanidine Carbonate | 6.500 |
| Succinic Acid | 0.250 |
| Tropaeolin "O" (Also known as, Acid Orange 6, sold by Pylam) | 0.0015 |
| Crodafos SG | 1.500 |

The pH of the relaxer base is 10.20.

The guanidine carbonate is present in the cream base in an amount of 0.0621 grams per milliliter. The density of the cream base is 0.956 grams per milliliter.

The relaxer base was prepared in a manner similar to that described in Example 1.

The activator lotion was the same composition as shown in Example 1.

The cream base and activator are mixed under ambient conditions in a weight ratio of 12.5 to 1, and the results are similar to those of Example 1.

The following illustrates that mixing errors of ±10% when estimating half the contents of either the cream base of the present invention or the activator of the present invention result in minimal changes in the guanidine carbonate concentration in the mixture, and therefore minimal changes in the guanidine hydroxide concentration of the hair relaxer.

A typical two-component hair relaxer system of the present invention prepared in accordance with this example comprises 250 grams of cream base containing 6.5 weight% guanidine carbonate (0.090 moles) and 20 grams of activator lotion.

When the cream base and activator lotion prepared above are mixed in a weight ratio of 12.5 to 1 as set forth above, the corresponding volume ratio is 262 to 14.

When the full contents are mixed, the concentration of guanidine carbonate in the relaxer when the activator and base are mixed equal Cr (gm/ml).

$$Cr = \frac{Vb \times Cb}{Va + Vb} = \frac{262 \text{ ml} \times 0.0621 \text{ gm/ml}}{14 \text{ ml} + 262 \text{ ml}} = \frac{16.27}{276} = 0.0590 \text{ g/ml}$$

When half contents are measured accurately and mixed, the concentration of guanidine carbonate is the same.

Because the consumer may make an error of ±10% when estimating half the contents of either the cream base or the activator lotion, the following values could be expected.

First, assuming that the consumer employs 10% by volume less base than the true half content of base and 10% by volume more activator than the true half content of activator, a lower Cr is obtained as follows:

$$Cr = \frac{117.9 \text{ ml} \times 0.0621 \text{ gm/ml}}{7.7 \text{ ml} + 117.9 \text{ ml}} = 0.0583 \text{ g/ml}$$

Next, assuming that the consumer employs 10% by volume more base than the true half content of base and 10% by volume less activator than the true half content of activator, a higher Cr is obtained as follows:

$$Cr = \frac{144.1 \text{ ml} \times 0.0621 \text{ gm/ml}}{6.3 \text{ ml} + 144.1 \text{ ml}} = 0.0595 \text{ g/ml}$$

Thus, even with a ±10% error in the volume of cream base and a ±10% error in the volume of activator, the final concentration of guanidine carbonate in the relaxer is less than about ±2% from the desired value.

On the other hand, for a typical relaxer of the prior art where the cream base contains the calcium hydroxide and the liquid activator contains the guanidine carbonate, the following can be shown for a commercially available relaxer system designed to produce a guanidine carbonate concentration in the relaxer of 0.0646 g/ml. Such a relaxer system is comprised of the following cream base and liquid activator:

| $Ca(OH)_2$ Containing Cream Base | |
|---|---|
| | Wt % |
| Oil Phase | |
| Cosmowax J (Croda) (Cetearyl Alcohol, Ceteareth-20) | 10.00 |
| Aldol 52 (Sherex Chemical Co., Inc., Duplin, Ohio) (Cetyl Alcohol) | 2.00 |
| Light Mineral Oil (Witco Corp., Melrose Park, IL) (Mineral Oil) | 20.00 |
| Water Phase | |
| Deionized Water | 49.79 |
| Propylene Glycol | 5.00 |
| Fluilan AWS (Croda) (PPG-12 PEG-65 Lanolin Oil) | 3.00 |
| Calcium Hydroxide | 5.21 |
| Duponol XL (DEA-Lauryl Sulfate, Sodium Lauramino-propionate, DEA-Lauraminopropionate) | 5.00 |

The $Ca(OH)_2$ containing cream base has a density of 1.013 grams per milliliter, and is used in an amount of 218 grams corresponding to a volume of 215 milliliters.

| Guanidine Carbonate Containing Liquid Activator | |
|---|---|
| | Wt % |
| Deionized Water | 75.49 |
| Keltrol (Kelco, San Diego, CA) | 0.50 |

| Guanidine Carbonate Containing Liquid Activator | |
|---|---|
| | Wt % |
| (Xanthan Gum) | |
| Guanidine Carbonate | 24.00 |
| FD&C Yellow #5 | 0.007 |
| FD&C Red #4 | 0.005 |

The guanidine carbonate is present in the liquid activator in an amount of 0.2611 grams per milliliter, and the activator has a density of 1.088 g/ml. The liquid activator is used in an amount of 77 grams, corresponding to a volume of 71 milliliters.

Thus, when the full contents are mixed the concentration of guanidine carbonate in the relaxer (Cr) is as follows:

$$Cr = \frac{Va \times Ca}{Va + Vb} = \frac{71 \text{ ml} \times 0.2611 \text{ gm/ml}}{71 \text{ ml} + 215 \text{ ml}} = 0.0646 \text{ g/ml}$$

When half contents are measured accurately and mixed, the concentration of guanidine carbonate is the same:

$$Cr = \frac{35.5 \text{ ml} \times 0.2611 \text{ gm/ml}}{35.5 \text{ ml} + 107.5 \text{ ml}} = 0.0646 \text{ g/ml}$$

Because the consumer may make an error of ±10% when estimating half of the contents of either the cream base or the liquid activator, the following values could be expected.

First, assuming that the consumer employs 10% by volume less base than the true half contents of base and 10% by volume more activator than the true half contents of activator, a higher Cr is obtained as follows:

$$Cr = \frac{39.05 \text{ ml} \times 0.2611 \text{ gm/ml}}{39.05 \text{ ml} + 96.25 \text{ ml}} = 0.0749 \text{ g/ml}$$

Next, assuming that the consumer employs 10% by volume more base and 10% by volume less activator than the true half contents, a lower Cr is obtained as follows:

$$Cr = \frac{31.95 \text{ ml} \times 0.2611 \text{ gm/ml}}{31.95 \text{ ml} + 118.25 \text{ ml}} = 0.0554 \text{ g/ml}$$

Thus, with a ±10% error in the volume of cream base and a ±10% error in the volume of activator, the final concentration of guanidine carbonate in the relaxer is approximately ±15% from the desired value. Such a variation in the strength of the relaxer is significant and can lead to highly over-processed hair with an increase in hair damage and irritation or highly underprocessed hair.

A group of 25 women who were currently users of the above commercially available product reported significantly less tingling, stinging and burning on the skin and scalp with a relaxer composition prepared in accordance with this example than with the commercially available product they had been employing.

EXAMPLE 3

A two-component hair relaxer system according to the present invention was formulated, with one component being in the form of a cream base and the other component being in the form of a powder. The components had the following composition.

| Formulation of Relaxer Base Containing Guanidine Carbonate. | |
|---|---|
| | Weight % |
| Oil Phase | |
| Cetyl alcohol | 4.80 |
| Stearyl alcohol | 5.20 |
| Steareth-20 | 1.00 |
| Mineral oil | 10.00 |
| Petrolatum | 10.00 |
| Steareth-10 | 1.00 |
| Water Phase | |
| Deionized Water | 59.01 |
| Fluilan AWS | 3.00 |
| Disodium EDTA | 0.20 |
| Guanidine Carbonate | 5.59 |
| Succinic Acid | 0.2 |

The pH of the relaxer base is 10.28.

The relaxer base was prepared in a manner similar to that described in Example 1.

The activator powder has the following composition and was prepared by wet/dry blending followed by sieving with a 200 mesh sieve.

| | Wt. % |
|---|---|
| Calcium Hydroxide powder | 88.0 |
| Caprylyl Pyrrolidone | 12.0 |
| (Surfadone LP100 sold by ISP Inc.) | |
| | 100.0 |

The cream base and activator powder are mixed under ambient conditions in a weight ratio of 20 to 1, and the results are similar to those of Example 1.

EXAMPLE 4

A two-component hair relaxer system according to the present invention was formulated, with one component being in the form of a cream base containing a non-polymeric conditioner, and the other component being in the form of a powder.

| Formulation of Relaxer Base Containing Guanidine Carbonate. | |
|---|---|
| Ingredient | Weight % |
| Oil Phase | |
| Cetyl alcohol | 3.52 |
| Stearyl alcohol | 3.81 |
| Steareth-20 | 0.74 |
| Mineral oil | 9.74 |
| Petrolatum | 9.74 |
| Steareth-10 | 1.00 |
| Water Phase | |
| Deionized Water | 58.92 |
| Fluilan AWS | 2.46 |
| Arquad 2HT-75 (Quaternium-18 and Isopropyl alcohol) | 1.50 |
| Guanidine Carbonate | 6.99 |
| Succinic Acid | 0.2 |
| Crodafos SG | 1.64 |

The pH of the relaxer base is 10.28.

The relaxer base was prepared in a manner similar to that described in Example 1.

The activator was commercial powdered calcium hydroxide.

The cream base and activator are mixed under ambient conditions in a weight ratio of 24 to 1, and the results are similar to those of Example 1.

The relaxer is tested for efficacy of relaxation and reversion according to the following procedure.

Swatches of hair are prepared containing 20 to 40 hairs bound at the proximal end with waterproof tape.

For each test, 3 swatches are attached to the surface of a glass plate.

The relaxer is applied to the hair, using long strokes to fully extend the hair. Each swatch is stroked with a soft camel's hair brush every 5 to 10 minutes until the relaxer has been on the hair for the appropriate amount of time for the relaxer which is being tested.

The relaxer is then rinsed from the hair and glass plate with tap water.

A 50:50 blend of neutralizing shampoo and water then is carefully applied to the hair. The neutralizing shampoo mixture is kept in constant contact with the hair for at least 3 minutes. Each swatch is rinsed with water to remove the neutralizing shampoo.

Each swatch is attached loosely to a glass rod with a cotton thread and dried with a hair dryer set on cool for 1 hour.

The swatches are then removed from the glass rods. The bound end of the relaxed swatches is attached to alligator clips positioned at a zero line on a finely divided graph paper. The graphs are placed in a vertical position and equilibrated to room temperature and 65% relative humidity (RH) for 1 hour.

A pressure sensitive label is attached to the hair so that the upper edge of the label marks a point that is 10 to 15 cm from the bottom of the tape that binds the swatch. This point is recorded as the initial length (Lr).

With the label holding hairs together, the hair is gently pulled until it is fully extended but not stretched. The point marked by the upper edge of the label used to hold the hair is recorded as the extended length (Ls).

The hair is then cut along the upper edge of the label.

Each graph is placed in a vertical position inside a constant-humidity chamber maintained at 90% RH for 24 hours.

After 24 hours, each graph is removed from the humidity chamber and the swatches are allowed to equilibrate to room temperature and 65% RH for 1 hour. The length of each swatch (Lv) is recorded without touching the hair.

The % relaxation and % reversion are calculated as follows:

1) $\% \text{ Relaxation} = 100 \times \left(1 - \frac{Ls - Lr}{Ls}\right)$ where $Ls$ = extended length
$Lr$ = original length 2) $\% \text{ Reversion} = \left[\% \text{ relaxation} - \left(100 \times \left(1 - \frac{Ls - Lc}{Ls}\right)\right)\right]$ where $Ls$ = initial extended length
$Lc$ = length after reversion The relaxer was subjected to two relaxation/reversion tests, and the data for each test is shown below.

|  | Relaxation % | Reversion % |
| --- | --- | --- |
| Test No. 1 | 97.8 ± 0.0 | 1.1 ± 1.1 |
| Test No. 2 | 98.5 ± 0.5 | 0.0 ± 0.0 |

EXAMPLE 5

A two-component hair relaxer system according to the present invention was formulated with one component being in the form of a cream base containing a polymeric conditioner, and the other component being in the form of commercial calcium hydroxide powder.

The components had the following composition.

| Formulation for Relaxer Base Containing Guanidine Carbonate without Acidulant/buffer and without color indicator | |
| --- | --- |
| Ingredient | Wt % |
| Oil Phase | |
| Cetyl alcohol | 3.26 |
| Stearyl alcohol | 3.53 |
| Steareth-10 | 0.68 |
| Steareth-20 | 0.68 |
| Mineral oil | 8.00 |
| Petrolatum | 8.00 |
| Water Phase | |
| Water | 55.78 |
| Propylene glycol | 3.77 |
| Fluilan AWS | 2.28 |
| Guanidine carbonate | 5.59 |
| Duponol XL | 1.51 |
| Polyquaternium-2 (Mirapol A-15, sold by Miranol Inc.) | 3.02 |

In preparing the above relaxer base composition, the oil phase is prepared as in Example 1. The water, propylene glycol and Fluilan AWS are heated quickly to 70° C., and the heated oil phase is then added to these ingredients slowly with moderate homogenization. The mixture is left to cool, and when the mixture reaches 60° C., homogenizing is continued while Mirapol A-15 is added. When the mixture reaches 45° C., guanidine carbonate is added.

The activator comprises commercial powdered calcium hydroxide.

To form the hair relaxer, the cream base and the activator are admixed under ambient conditions in a weight ratio of 96:4 of cream base to activator.

EXAMPLE 6

The procedure of Example 5 was repeated, except that various acids as shown in the Table below were added to the relaxer base formulation of Example 5.

A mole ratio of 0.1:1 acid to guanidine carbonate was maintained for each relaxer base.

The pH of the relaxer base was determined based on a 10-minute immersion of a gel-filled combination electrode in the relaxer base formulation.

Each relaxer base was tested for efficacy of relaxation and reversion according to the procedure set forth in Example 4 above.

EVALUATION OF RELAXER-BASE FORMULATIONS CONTAINING GUANIDINE CARBONATE AND VARIOUS ACIDS

| Sample No. | Proton Source | pH | Relaxation % | Reversion % |
|---|---|---|---|---|
| 1 | — | 11.0 | 97.8 ± 0.0 | 5.8 ± 5.4 |
| 2 | Lactic acid | 10.7 | 97.0 ± 0.5 | 5.8 ± 3.1 |
| 3 | Tartaric acid | 10.3 | 96.5 ± .02 | 11.4 ± 5.8 |
| 4 | Ascorbic acid | 10.3 | 95.1 ± 0.3 | 12.0 ± 6.4 |
| 5 | Maleic acid | 10.3 | 97.2 ± 0.3 | 1.3 ± 1.1 |
| 6 | Glutamic acid | 10.4 | 97.7 ± 0.2 | 4.9 ± 1.6 |
| 7 | Succinic acid | 10.4 | 97.4 ± 0.6 | 3.7 ± 2.4 |

The headspace above Sample 1 had a slight ammonia odor. This odor became more intense when the formulation was stirred. In contrast, no ammonia odor was noted in Sample Nos. 2 to 7.

Samples 3 and 4 had an acceptable relaxation efficacy, but reversion for these samples was more than 10%. Although these samples provide acceptable relaxation, they are not preferred because of their higher reversion. Samples 5 to 7 provided good relaxation and low reversion.

EXAMPLE 7

A liquid activator containing guanidine carbonate is prepared for use with a $Ca(OH)_2$ containing cream base. The liquid activator has the following composition.

| Guanidine carbonate | 25 gm |
|---|---|
| Succinic Acid | 1.64 gm |
| Water | 73.36 gm |

EXAMPLE 8

A liquid activator containing guanidine carbonate is prepared for use with a $Ca(OH)_2$ containing cream base. The liquid activator has the following composition.

| Guanidine carbonate | 25 gm |
|---|---|
| Glutamic acid | 2.04 gm |
| Water | 72.96 gm |

It will be understood that the above description of the present invention is susceptible to various modifications, changes and adaption, and the same are intended to be comprehended within the meaning and range of equivalents of the appended claims.

What is claimed is:

1. A two-component hair relaxer system for producing an alkaline hydroxide relaxer for relaxing hair comprising:
   (a) a first component comprising a water-containing cream base containing a water-soluble salt of a relatively strong base selected from the group consisting of quanidine and N-methyl guanidine with an anion capable of being precipitated by an alkaline earth metal ion under highly alkaline conditions, and
   (b) a second, separate component, which is substantially free of water, and containing an alkaline material which is an alkaline earth metal hydroxide, an alkaline earth metal oxide, or a mixture thereof having an alkaline earth metal ion which forms a precipitate with the anion when the first component and second component are mixed.

2. The relaxer system according to claim 1, wherein the anion of the water-soluble salt is selected form the group consisting of carbonate, sulfate, sulfite, phosphate, fluoride, oxalate, tartrate, laurate and alginate.

3. The relaxer system of claim 1, wherein the water-soluble salt is guanidine carbonate.

4. The relaxer system of claim 1, wherein the water-soluble salt is present in the water base in an amount of 1 to 20% by weight of the cream base.

5. The relaxer system according to claim 1, wherein the water-soluble salt is present in the cream base in an amount of from about 1 to about 10% by weight of the cream base.

6. The relaxer system according to claim 1, wherein the water-soluble salt is present in the cream base in an amount of from about 6 to about 8% by weight of the cream base.

7. The relaxer system according to claim 1, wherein the cream base contains a conditioning agent.

8. The relaxer system according to claim 7, wherein the conditioning agent is present in an amount of about 0.1 to about 4% by weight of the cream base.

9. The relaxer system according to claim 7, wherein the conditioning agent is a non-polymeric quaternary nitrogen containing compound.

10. The relaxer system according to claim 1, wherein the alkaline material is calcium hydroxide, calcium oxide or a mixture thereof.

11. The relaxer system according to claim 1, wherein the second component contains less than about 20 weight percent water.

12. The relaxer system according to claim 1, wherein the second component contains less than 10% by weight water.

13. The relaxer system according to claim 1, wherein the second component is anhydrous.

14. The relaxer system according to claim 1, wherein the second component is a pourable suspension which contains 20 to 60 weight percent of the alkaline material.

15. The relaxer system according to claim 1, wherein the second component contains a water-miscible, hydrophilic liquid carrier.

16. The relaxer system according to claim 15, wherein the liquid carrier is a polyhydroxy compound or an ether.

17. The relaxer system according to claim 15, wherein the liquid carrier is selected from the group consisting of propylene glycol, glycerine, butylene glycol and hexylene glycol.

18. The relaxer system according to claim 1, wherein the second component is a powder.

19. The relaxer system according to claim 18, wherein alkaline material is present in the powder in an amount of 20 to 100% by weight of the powder.

20. The relaxer system according to claim 1, wherein the alkaline material is present in the second component in an amount sufficient to provide a molar excess of from 5 to 200% with respect to the water-soluble salt of the cream base.

21. The relaxer system according to claim 1, wherein the volume ratio of the second component to the first component is from one part by volume second component to about 8 to 50 parts by volume first component.

22. The relaxer system according to claim 21, wherein the volume ratio of the second component to the first component is from one part by volume second component to about 10 to 25 parts by volume first component.

23. The relaxer system according to claim 1, wherein the density of the second component is from about 1.4 gm/ml to about 2.34 gm/ml.

24. The relaxer system according to claim 1, wherein the weight ratio of second component to first component is from one part by weight second component to about 6 to 30 parts by weight first component.

25. The relaxer system according to claim 1, wherein the weight ratio of second component to first component is from one part by weight second component to about 10 to 15 parts by weight first component.

26. The relaxer system according to claim 1, wherein the water-soluble salt is a salt of relatively strong organic nitrogen containing base with a carbonate anion and which is susceptible to alkaline hydrolysis and formation of ammonia, and wherein the first component contains a carbonate/bicarbonate buffer to retard decomposition of the water-soluble salt and formation of ammonia.

27. The relaxer system according to claim 26, wherein the buffer provides the cream base with a pH of from about 9.5 to about 10.5.

28. The relaxer system according to claim 27, wherein an acid which does not interfere with the relaxing is present in the cream base to form the buffer and provide the pH of from about 9.5 to about 10.5.

29. The relaxer system according to claim 28, wherein the acid is one which does not cause a degree of reversion of greater than about 15%.

30. The relaxer system according to claim 28, wherein the acid is an organic acid.

31. The relaxer system according to claim 28, wherein the acid is at least one acid selected from the group consisting of an aliphatic acid, an alicyclic acid, an aromatic acid and a heterocyclic acid.

32. The relaxer system according to claim 28, wherein the acid is at least one acid selected from the group consisting of a monocarboxylic acid and a dicarboxylic acid.

33. The relaxer system according to claim 28, wherein the acid is at least one acid selected from the group consisting of an aliphatic monocarboxylic acid and an aliphatic dicarboxylic acid.

34. The relaxer system according to claim 28, wherein the acid is at least one acid selected from the group consisting of succinic acid, maleic acid, oxalic acid, glutamic acid and lactic acid.

35. The relaxer system according to claim 28, wherein the acid is at least one acid selected from the group consisting of succinic, maleic acid, and glutamic acid.

36. The relaxer system according to claim 28, wherein the acid is succinic acid.

37. The relaxer system according to claim 28, wherein the acid is glutamic acid.

38. The relaxer system according to claim 28, wherein the acid is an inorganic acid.

39. The relaxer system according to claim 28, wherein the acid is sulfuric acid or phosphoric acid.

40. The relaxer system according to claim 28, wherein the acid contains at least one substituent selected from the group consisting of an amino group and a hydroxy group.

41. The relaxer system according to claim 28, wherein the acid is present in an amount of from about 2 to 20 mol % of the number of mols of water-soluble salt.

42. The relaxer system according to claim 28, wherein the acid is present in an amount of from 5 to 10 mol % of the number of mols of water-soluble salt.

43. The relaxer system according to claim 27, wherein the first component contains a pH indicator.

44. The relaxer system according to claim 43, wherein the pH indicator is present in an amount of from 0.0005 to 0.5% by weight of the first component.

45. The relaxer system according to claim 43, wherein the pH indicator is selected from the group consisting of Tropaeolin "O", Thiazole Yellow "G", Eosin I, Pourriers Blue, Mordant Blue #1, Mordant Red #3 and External D&C Violet #2.

46. A process for producing a hair relaxer composition for relaxing hair comprising mixing the first component and second component of claim 1.

47. A hair relaxer composition comprising the mixture resulting from admixing the first component and second component of claim 26.

48. A two-component hair relaxing system for producing an alkaline hydroxide relaxer for relaxing hair comprising:
(a) a first component comprising a liquid activator comprising a water-solution of a water-soluble salt of a relatively strong organic nitrogen containing base selected from the group consisting of guanidine and N-methyl guanidine with a carbonate anion and which is susceptible to alkaline hydrolysis and formation of ammonia, wherein the water-solution contains a carbonate/bicarbonate buffer to retard decomposition of the water-soluble salt and formation of ammonia, and
(b) a cream base which contains an alkaline material which is an alkaline earth metal hydroxide having an alkaline earth metal ion which forms a precipitate with the carbonate anion, the first component when subsequently mixed with the second component reacting with the alkaline material to produce a hair relaxer composition.

49. A two-component hair relaxing system according to claim 48, wherein the water-soluble salt is guanidine carbonate and the alkaline material is calcium hydroxide.

50. A two-component hair relaxing system according to claim 48, wherein the water-soluble salt is present in the first component in an amount of about 20 to about 30% by weight of the first component, and the alkaline material is present in the second component in an amount of about 4 to about 7% by weight of the second component.

51. A two component hair relaxer system according to claim 1, wherein the water-soluble salt is guanidine carbonate and is present in the cream base in an amount of about 6 to about 8% by weight of the cream base, and the alkaline material is calcium hydroxide and is present in an amount sufficient to provide a molar excess of from 5 to 200% with respect to the guanidine carbonate.

52. A two component hair relaxer system according to claim 51, wherein the first component contains a carbonate/bicarbonate buffer to retard decomposition of the guanidine carbonate and formation of ammonia.

53. A two component hair relaxer system according to claim 52, wherein an acid which does not interfere with the relaxing process is present to form the buffer and provide a pH of from about 9.5 to 10.5.

54. A two component hair relaxer system according to claim 53, wherein the acid is at least one acid selected from the group consisting of a monocarboxylic acid and a dicarboxylic acid.

55. A two component hair relaxer system according to claim 53, wherein the acid is at least one acid selected from the group consisting of succinic acid, maleic acid and glutamic acid.

56. A two component hair relaxer system according to claim 51, wherein the weight ratio of second component to first component is from one part by weight second component to about 6 to 30 parts by weight first component.

* * * * *